(12) United States Patent
Grajales et al.

(10) Patent No.: US 9,205,408 B2
(45) Date of Patent: Dec. 8, 2015

(54) CATALYST FOR ALDOL CONDENSATION

(71) Applicant: Celanese International Corporation, Irving, TX (US)

(72) Inventors: Gustavo Angel Robelo Grajales, Coatzacoalcos (MX); Ricardo Alderete Delgadillo, Coatzacoalcos (MX)

(73) Assignee: Celanese International Corporation, Irving, TX (US)

( * ) Notice: Subject to any disclaimer, the term of this patent is extended or adjusted under 35 U.S.C. 154(b) by 0 days.

(21) Appl. No.: 14/458,646

(22) Filed: Aug. 13, 2014

(65) Prior Publication Data

US 2015/0051425 A1    Feb. 19, 2015

Related U.S. Application Data

(60) Provisional application No. 61/865,449, filed on Aug. 13, 2013.

(51) Int. Cl.

| | | |
|---|---|---|
| *C07C 45/72* | (2006.01) | |
| *B01J 23/00* | (2006.01) | |
| *B01J 21/16* | (2006.01) | |
| *C07C 45/64* | (2006.01) | |
| *B01J 37/04* | (2006.01) | |
| *B01J 37/06* | (2006.01) | |
| *B01J 23/02* | (2006.01) | |
| *B01J 35/02* | (2006.01) | |
| *B01J 37/00* | (2006.01) | |
| *C07C 49/04* | (2006.01) | |
| *B01J 35/10* | (2006.01) | |

(52) U.S. Cl.
CPC .................. *B01J 21/16* (2013.01); *B01J 23/02* (2013.01); *B01J 35/023* (2013.01); *B01J 35/026* (2013.01); *B01J 37/0009* (2013.01); *B01J 37/04* (2013.01); *B01J 37/06* (2013.01); *C07C 45/64* (2013.01); *C07C 45/72* (2013.01); *C07C 49/04* (2013.01); *B01J 35/1061* (2013.01); *B01J 35/1066* (2013.01)

(58) Field of Classification Search
CPC ............ C07C 45/72; B01J 23/02; B01J 23/92
USPC .......................................... 568/388; 502/341
See application file for complete search history.

(56) References Cited

U.S. PATENT DOCUMENTS

| | | | |
|---|---|---|---|
| 2,130,592 | A | 9/1938 | McAllister et al. |
| 2,827,490 | A | 3/1958 | Martin |
| 2,879,298 | A | 3/1959 | Seligman |
| 2012/0135860 | A1 | 5/2012 | Carlsson et al. |

FOREIGN PATENT DOCUMENTS

GB         688207         3/1953

OTHER PUBLICATIONS

International Search Report and Written Opinion for corresponding PCT/US2014/050871 mailed Oct. 27, 2014.

*Primary Examiner* — Sikarl Witherspoon

(57) ABSTRACT

In one embodiment, the invention is to a catalyst composition comprising lime and cement. Preferably, the catalyst composition comprises the lime and the cement in a weight ratio of at least 3.5:1 respectively.

20 Claims, 1 Drawing Sheet

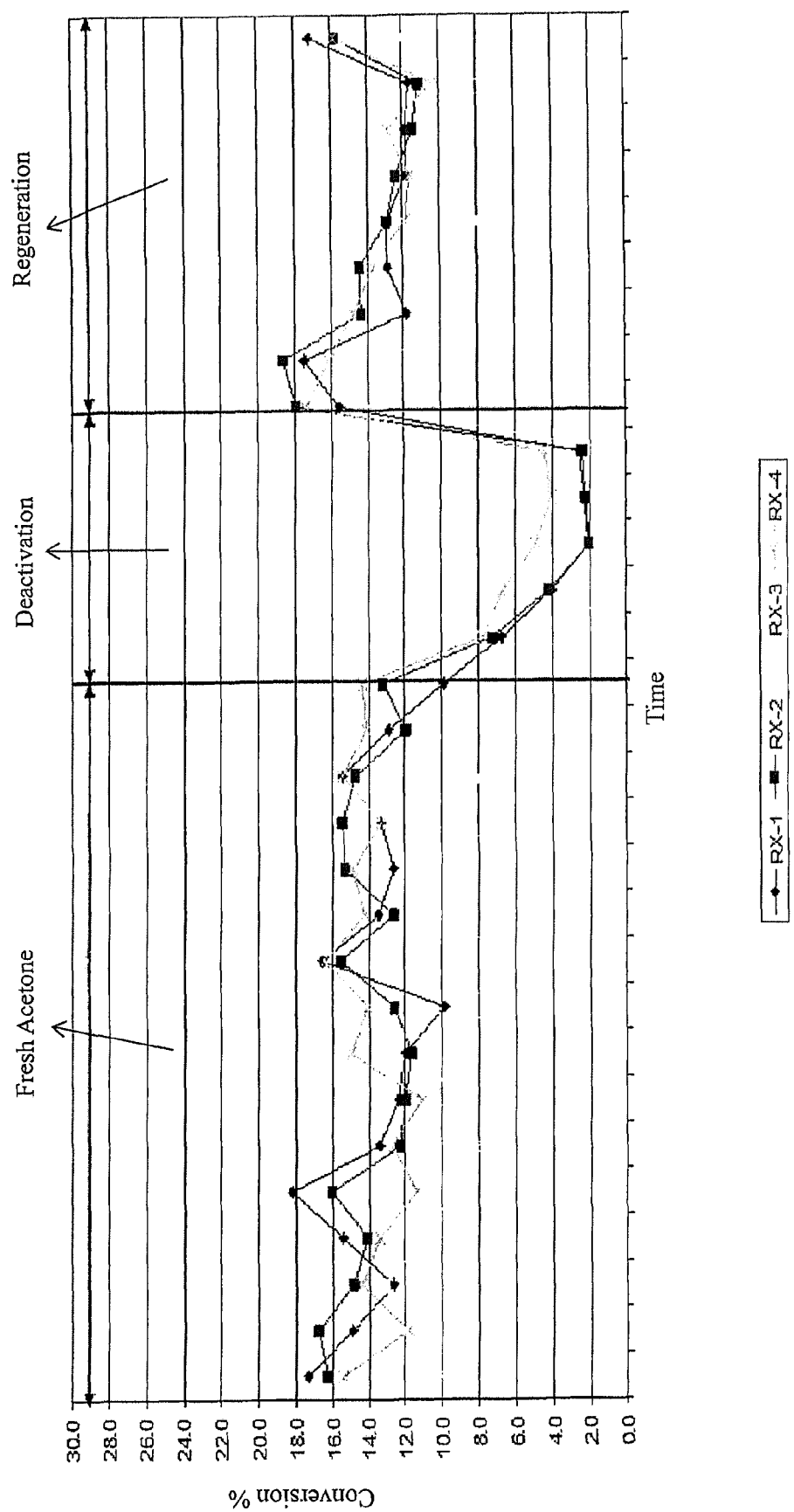

__US 9,205,408 B2__

CATALYST FOR ALDOL CONDENSATION

CROSS-REFERENCE TO RELATED APPLICATION

This application claims priority to U.S. Provisional Application No. 61/865,449 filed on Aug. 13, 2013, the entirety of which is incorporated herein by reference.

FIELD OF THE INVENTION

The present invention relates generally to aldol condensation. More specifically, the present invention relates to a catalyst for use in aldol condensation reactions.

BACKGROUND OF THE INVENTION

Aldol condensation is an organic reaction in which an enol or an enolate ion reacts with a carbonyl compound to form a β-hydroxyaldehyde or β-hydroxyketone, followed by a dehydration to give a conjugated enone. Specifically, the first part of the aldol condensation reaction is an aldol reaction and the second part is an elimination reaction (e.g., dehydration that involves removal of a water molecule or an alcohol molecule). Because β-hydroxyaldehydes, β-hydroxyketones, and enones have long been valued commercially, many methods of production have been developed. One exemplary aldol condensation production process utilizes the catalyzed condensation of acetone or dimethyl ketone (DMK) to obtain diacetone alcohol (DAA), and the dehydration of the DAA to yield mesityl oxide (MO). DAA is an industrially important compound that is mainly used as a solvent in purification processes. MO is a useful compound with various applications, including its use as a precursor to the industrial solvent, methyl isobutyl ketone (MIBK).

Aldol condensation reactions are often conducted in the presence of a catalyst composition. For example, the aldol condensation of acetone is commonly conducted in the presence of a base catalyst composition comprising an active phase including NaOH, KOH, $Ca(OH)_2$, and/or $Ba(OH)_2$. Many other alternative catalyst active phases exist such as metal oxides and hydroxides, which exhibit both acidic and basic properties, with varying degrees of selectivity towards DAA. Furthermore, the catalyst composition commonly includes at least one of the aforementioned active phases affixed to a support formed from carbon, alumina, and/or sodium metasilicate. However, these catalyst compositions can be expensive and have been known to exhibit only low to moderate conversion and regeneration when used in aldol condensation reactions.

Thus, the need exists for improved processes for performing low cost aldol condensation reactions, and for improved catalysts capable of providing high enol or enolate ion conversions in the formation of β-hydroxyaldehydes or β-hydroxyketones, and high selectivity for β-hydroxyaldehydes, β-hydroxyketones, and/or conjugated enones.

SUMMARY OF THE INVENTION

In one embodiment, the present invention is to a catalyst composition comprising an active phase comprising lime and a support comprising cement. Preferably, the catalyst composition comprises the lime and the cement in a weight ratio of at least 3.5:1 respectively. The lime may comprise calcium hydroxide and the cement may be portland cement. The catalyst composition may further comprise water. In one embodiment, the catalyst composition comprises particles and the particles have a particle size between about −7/+20 mesh. In some embodiments, the inventive catalyst composition is in amorphous form.

In another embodiment, the present invention is to a process for producing the above-mentioned catalyst composition. The process comprises the step of mixing lime and cement while providing a predetermined amount of water to form a catalyst precursor mixture. Preferably, the mixing comprises the step of adding the lime and the cement at a weight ratio of at least 3.5:1 respectively. The process further comprises the step of drying the catalyst precursor mixture to form the catalyst composition comprising an active phase comprising the lime and a support comprising the cement.

In another embodiment, the present invention is to a process for producing diacetone alcohol. The process comprises the step of reacting acetone over a catalyst composition and under conditions effective to form a crude diacetone alcohol composition. Preferably, the catalyst composition comprises an active phase comprising lime and a support comprising cement in a weight ratio of at least 3.5:1 respectively.

In yet another embodiment, the present invention is to a process for producing diacetone alcohol. The process comprises the step of adding lime and cement into a mixer at a weight ratio of at least 3.5:1 respectively. The process further comprises the step of mixing the lime and the cement while providing a predetermined amount of water to form a catalyst precursor mixture. The process further comprises the step of drying the catalyst precursor mixture to form a catalyst composition comprising an active phase comprising the lime and a support comprising the cement. The process further comprises the step of reacting acetone over the catalyst composition and under conditions effective to form a crude diacetone alcohol composition.

BRIEF DESCRIPTION OF DRAWINGS

The invention is described in detail below with reference to the appended drawings, wherein like numerals designate similar parts.

FIG. 1 is a graph showing conversions achieved using the process of the present invention.

DETAILED DESCRIPTION OF THE INVENTION

Introduction

Production of β-hydroxyaldehydes or β-hydroxyketones, such as DAA, via most conventional aldol condensation processes has been limited by economic and environmental constraints. Conventional processes for producing DAA comprises the aldol condensation of acetone in the presence of a base catalyst composition comprising an active phase including NaOH, KOH, $Ca(OH)_2$, and/or $Ba(OH)_2$. The catalyst composition commonly includes at least one of the aforementioned active phases affixed to a support formed from carbon, alumina, and/or sodium metasilicate. However, these catalyst compositions can be expensive and have been known to exhibit only low to moderate conversion and regeneration when used in aldol condensation reactions. As a result, use of these catalyst compositions in commercial manufacturing can significantly increase the time and costs associated with the commercial production of β-hydroxyaldehydes or β-hydroxyketones, such as DAA, and/or the conjugated enones thereof, such as MO.

Catalyst Composition

In one embodiment, the present invention is to a catalyst composition comprising an active phase comprising lime and a support comprising cement. Specifically, it has now been discovered that the use of cement as the primary element of a support in the preparation of the catalyst, surprisingly and unexpectedly yields a catalyst composition that, when used in an aldol condensation, provides for significant improvement in reaction efficiencies. Conventionally, carbon, alumina, and/or sodium metasilicate are used as the primary element of a support in the preparation of a catalyst precursor mixture for an aldol condensation reaction. However, in preferred embodiments, the replacement of carbon, alumina, and/or sodium metasilicate that is conventionally used, with cement surprisingly provides for a catalyst composition that substantially maintains or provides for an increase in enol or enolate ion conversion in an aldol condensation reaction along with an increase in β-hydroxyaldehyde, β-hydroxyketone, and/or conjugated enone selectivity and regeneration of the inventive catalyst composition.

In some embodiments, the chemical characteristics of the active phase may comprise $Ca(OH)_2$ (i.e., calcium hydroxide, lime, or hydrated lime) from 82 wt % to 84 wt % $Ca(OH)_2$, e.g., preferably about 84.0 wt % $Ca(OH)_2$. Preferably, the active phase may further comprise water. As such, in some embodiments, the resultant active phase may comprise from 0.5 wt % to 1.0 wt % water, e.g., preferably about 1.0 wt % water. In some embodiments, the active phase may further comprise MgO (i.e., magnesium oxide). As such, in some embodiments, the resultant active phase may comprise from 0.1 wt % to 0.5 wt % MgO, e.g., preferably about 0.5 wt % MgO. In some embodiments, the active phase may further comprise $SiO_2$ (i.e., silica). As such, in some embodiments, the resultant active phase may comprise from 0.1 wt % to 0.5 wt % $SiO_2$, e.g., preferably about 0.5 wt % $SiO_2$. In some embodiments, the active phase may further comprise $Fe_2O_3$ and $Al_2O_3$ (i.e., iron and aluminum oxide). As such, in some embodiments, the resultant active phase may comprise from 0.1 wt % to 0.2 wt % $Fe_2O_3$ and $Al_2O_3$, e.g., preferably about 0.2 wt % $Fe_2O_3$ and $Al_2O_3$. Preferably, these limits and ranges apply to the active phase of the catalyst composition.

In one embodiment, the particle size distribution of the active phase is about 200 mesh, i.e., typically a maximum 94% of the particles of the active phase will be retained by a 200 mesh sieve. As a result, the active phase comprises substantially fine particles of lime.

In the preferred embodiment, the catalyst is a supported catalyst comprising a catalyst support in addition to the active phase comprising lime in the amounts indicated above. The total weight of the support, based on the total weight of the catalyst, preferably is from 20 wt % to 40 wt %, e.g., from 25 wt % to 35 wt % or from 25 wt % to 30 wt %. The support material is cement or portland cement comprising CaO from 64 wt % to 84 wt % CaO, e.g., preferably about 64 wt % CaO. In some embodiments, the cement or portland cement may further comprise $SiO_2$. As such, in some embodiments, the cement or portland cement may comprise from 21 wt % to 29 wt % $SiO_2$, e.g., preferably about 21 wt % $SiO_2$. In some embodiments, the cement or portland cement may further comprise $Al_2O_3$. As such, in some embodiments, the cement or portland cement may comprise from 4.5 wt % to 5.5 wt % $Al_2O_3$, e.g., preferably about 5.5 wt % $Al_2O_3$. In some embodiments, the cement or portland cement may further comprise $Fe_2O_3$. As such, in some embodiments, the cement or portland cement may comprise from 3.5 wt % to 4.5 wt % $Fe_2O_3$, e.g., preferably about 4.5 wt % $Fe_2O_3$. In some embodiments, the cement or portland cement may further comprise MgO. As such, in some embodiments, the cement or portland cement may comprise from 0.5 wt % to 2.4 wt % MgO, e.g., preferably about 2.4 wt % MgO. In some embodiments, the cement or portland cement may further comprise sulphates. As such, in some embodiments, the cement or portland cement may comprise from 1.2 wt % to 1.6 wt % sulfates, e.g., preferably about 1.6 wt % sulfates.

As will be appreciated by those of ordinary skill in the art, the chemical characteristics of the support material or cement preferably are selected such that the catalyst system is suitably active, selective and robust under the process conditions employed for the formation of the desired product, e.g., DAA and/or MO. In addition, the hydrated lime included in the catalyst of the invention may be dispersed throughout the support, coated on the outer surface of the support (egg shell), or decorated on the surface of the support. In some embodiments, the active sites may be anchored or applied to the surfaces of pores that are distributed throughout the cement and hence are surface sites available to the reactants but are distributed throughout the support.

In some embodiments, the present invention is to a catalyst comprising lime and cement. In preferable embodiments, the present invention is to a catalyst composition consisting essentially of the lime, the water, and the cement. In other words, the catalyst composition does not include additional components such as sodium hydroxide and/or kieselguhr (diatomaceous earth) as found in some traditional catalyst compositions. In alternative embodiments, the present invention is to a catalyst composition consisting of only the lime, the water, and the cement. As a result, the catalyst composition of the present invention is capable of achieving a rate of reaction, conversion, selectivity, and regeneration equal to or better than traditional aldolization base lime catalysts.

For example, without being bound by theory, it is believed that the use of a cement as the primary element for the support in the preparation of the catalyst composition may inter alia 1) improve contact time throughout the catalyst composition; 2) increase temperature conditions in the catalyst composition; and/or 3) the cement may provide active basic $Ca(OH)_2$—Ca-silicate sites that contributed to additional conversion (as should be understood in some embodiments of the present invention the support comprising the cement may provide at least some conversion and selectivity properties). Specifically, with respect to the aldol condensation of acetone, the conversion of acetone is itself a function of temperature, such that temperature plays an important role in the evaluation of a catalyst used in the aldol condensation of acetone. Another variable that plays an important role in the evaluation of a catalyst used in the aldol condensation of acetone is contact time, which may be determined as the inverse of the space velocity. The catalyst composition of the present invention based mainly on the lime, the water and the cement operates more efficiently at a space velocity from $0.8\ hr^{-1}$ to $1.2\ hr^{-1}$ (mass) and a lower temperature such as between 5° C. and 15° C. than that of traditional catalyst compositions based mainly on lime and metasilicate (e.g., a support comprising primarily metasilicate). Even more advantageously, the catalyst composition of the present invention costs less to produce since catalysts based on silica and aluminum can have much higher prices, e.g., above 5 to 10 times higher than a catalyst composition based mainly on lime, water, and cement. Another advantage over supporting $Ca(OH)_2$ onto $SiO_2$ is that in supporting $Ca(OH)_2$ onto $SiO_2$ some of the added $Ca(OH)_2$ may be lost forming Ca silicates on the surface of the support, and may not remain as supported $Ca(OH)_2$, which could have higher activity than the Ca silicates formed on the surface.

Catalyst Preparation

In one embodiment, the inventive catalyst is formed by a process comprising the step of mixing lime and cement while providing a predetermined amount of water to form a catalyst precursor mixture. The process further comprises the step of drying the catalyst precursor mixture to form the catalyst composition comprising an active phase comprising the lime and a support comprising the cement. The formation of the catalyst precursor mixture may be achieved by adding the lime and the cement at a weight ratio of at least 3.5:1 respectively, more preferably in a range from 3.8:1 to 4.2:1, and even more preferable at a weight ratio of about 4:1. Specifically, it has now been discovered that the lime and the cement at a weight ratio of at least 3.5:1, surprisingly and unexpectedly yields a catalyst composition that, when used in an aldol condensation, provides for significant improvement in reaction efficiencies. For example, without being bound by theory, it is believed that the lime and the cement at a weight ratio of at least 3.5:1 may inter alia 1) increase surface area of the catalyst composition and therefore contact time throughout the catalyst composition; and/or 2) increase temperature conditions in the catalyst composition.

In one embodiment, the drying is performed for about 14-19 hours at a temperature between about 80° C. and 160° C. Preferably, the drying is performed for about 18 hours at a temperature between about 110° C. and 130° C.

In one embodiment of the present invention, the catalyst composition is formed by sieving the dried catalyst composition between meshes 7 (e.g., a sieve size of 2.8 mm) and 120 (e.g., a sieve size of 0.125 mm) to obtain a catalyst with a particle size between about −7/+20 mesh. In other words, about 90% of the dried catalyst composition will pass through a 7 mesh and be retained by a 20 mesh. As a result, the particle size distribution of the obtained catalyst composition comprises a larger surface area than compared to conventional catalyst compositions comprising carbon, alumina, and/or sodium metasilicate supports which typically have a particle size between about −80/+200 mesh (i.e., a finer material as compared to the cement material of the present invention). Advantageously, the replacement of the carbon, alumina, and/or sodium metasilicate that is conventionally used, with cement surprisingly provides for a catalyst that substantially maintains or provides for an increase in enol or enolate ion conversion in an aldol condensation reaction along with an increase in β-hydroxyaldehydes, β-hydroxyketones, and/or conjugated enone selectivity and regeneration of the inventive catalyst composition.

In some embodiments, the catalyst composition of the present invention is formed with porosity in the domains of mesoporosity, e.g., pores with a diameter from 2 nm to 50 nm and/or macroporosity, e.g., pores with a diameter of greater than 50 nm. In addition, the catalyst composition, in some embodiments, with the porosity in the domains of mesoporosity and/or macroporosity may be used in a fixed bed reactor for forming the desired product, e.g., DAA or MO.

In some embodiments, the catalyst composition of the present invention may be formed into shaped units, e.g., granular, extrudate, and amorphous forms, typically having maximum and minimum dimensions in the range from 0.5 mm to 2.8 mm, preferably from 0.85 mm to 2.4 mm. Preferably, the catalyst composition of the present invention with porosity in the domains of mesoporosity and/or macroporosity is obtained in the amorphous form, which is constituted by non-crystalline particles of solid (e.g., the cement), which facilitates the diffusion of reagents during use of the catalyst composition in aldol condensation processes.

The forming operations of the present invention may be carried out using conventional techniques, which are known to the skilled person (e.g., an impregnation technique may be employed, where the support may be shaped after impregnation). Alternatively, the catalyst composition may be shaped at any suitable stage in the production of the catalyst. The catalyst composition also may be effective in other forms, e.g., powders or small beads and may be used in these forms. In one embodiment, the catalyst may be used in a fluidized bed reactor. In this instance, the catalyst may be prepared via spray drying or spray thermal decomposition.

In embodiments where the catalyst is in a granular form, the catalyst composition may be formed by mixing (e.g., in an industrial blender) the lime with the cement (e.g., 240 g of lime and 60 g of cement (e.g., a weight ratio of 4:1 respectively)), and gradually adding small amounts of water, (e.g., 10-20 g of water at a time for a total of about 100-120 g of water) to obtain a granulated material. The resultant granulated material may then be dried by placing the granulated material on a rack or tray in an oven at a between about 80° C. and 160° C. for about 18 hours.

In embodiments where the catalyst is in an extrudate form, the catalyst composition may be formed by mixing (e.g., in an industrial blender) the lime with the cement (e.g., 240 g of lime and 60 g of cement (e.g., a weight ratio of 4:1 respectively)), and gradually adding small amounts of water (e.g., 25-35 g of water at a time for a total of about 150-170 g of water) to obtain a paste material. The paste material may then be extruded (e.g., in an industrial extruder) to generate an elongated material (e.g., elongated cylinders of material) comprising the catalyst composition. The resultant elongated material may then be dried by placing the elongated material on a rack or tray in an oven at a temperature between about 80° C. and 160° C. for about 18 hours.

In embodiments where the catalyst is in an amorphous form, the catalyst composition may be formed by mixing (e.g., in an industrial blender) the lime with the cement (e.g., 240 g of lime and 60 g of cement (e.g., a weight ratio of 4:1 respectively)), and gradually adding small amounts of water (e.g., 15-25 g of water at a time for a total of about 140-160 g of water) to obtain a paste material. The resultant paste material may then be dried by placing the paste material on a rack or tray in an oven at a temperature between about 80° C. and 160° C. for about 18 hours.

Production of DAA

In other embodiments, the invention is to a process for producing DAA by the condensation of acetone or DMK. Preferably, the condensation of the acetone or DMK occurs in the presence of the inventive catalyst composition. Specifically, the catalyst composition including an active phase comprising the lime and a support comprising the cement at a weight ratio of at least 3.5:1 respectively, more preferably in a range from 3.8:1 to 4.2:1, and even more preferable at a weight ratio of about 4:1. In preferred embodiments, the catalyst composition is maintained at a constant volume throughout the aldol condensation reaction.

In some embodiments, the process for producing DAA may further comprise activating the catalyst composition prior to the condensation reaction step. For example, the catalyst composition may be activated by washing the catalyst composition with water, preferably distilled water, which is at a temperature between about 90° C. and 100° C., preferably at about 96° C., with an approximate flow of 8-10 ml/min (e.g., a flow with a space velocity of about 2.0 hr$^{-1}$ or a reaction volume of about 250 ml). The catalyst activation may be performed to remove $Na_2CO_3$ and Ca present in the absorption of $CO_2$ from the air or atmosphere, and thus recovering OH active centers in the catalyst composition.

In some embodiments, the process for producing DAA may further comprise adding the acetone or DMK to the catalyst composition to initiate and maintain the aldol condensation reaction. For example, fresh acetone or DMK may be added to the catalyst composition after the activation step to remove excess moisture from the catalyst composition, and to initiate and maintain the aldol condensation reaction. In preferred embodiments, the acetone may be added at a predetermined amount to maintain a space velocity between 0.8 $hr^{-1}$ and 1.2 $hr^{-1}$, preferably to maintain a space velocity of 1 $hr^{-1}$.

The fresh acetone or DMK may be fed, e.g., via a centrifugal pump, from a storage tank to a reactor containing the catalyst. The reactor may be any suitable reactor. Preferably, the reactor is a fixed bed reactor, but other reactors such as a continuous stirred tank reactor or a fluidized bed reactor, may be used. Residence time in the reactor may range from 0.6 hours to 2.0 hours, preferably from 0.8 hours to 1.25 hours. Reaction pressure is not particularly limited, and the reaction is typically performed near atmospheric pressure. In one embodiment, the reaction may be conducted at a pressure ranging from 0.0 kPa to 800 kPa, preferably from 100 kPa to 400 kPa.

In some embodiments, the aldol condensation reaction may be conducted at a temperature of at least 1° C., e.g., at least 5° C. In terms of ranges, the reaction temperature may range between 1° C. and 20° C., preferably between 5° C. and 15° C. In preferred embodiments, the aldol condensation reaction may be conducted at a temperature between 1° C. and 20° C., without light, and at a substantially low relative humidity, e.g., a relative humidity between 0% and 5%, preferably between 0.5% and 1.5%. The reactor may comprise a closed circuit system of ice water that maintains a relatively constant temperature. For example, ice water may circulate through a jacket surrounding the reactor to maintain the reaction temperature in isothermal conditions between 1° C. and 20° C.

In some embodiments, the process for producing DAA may further comprise regenerating the inventive catalyst composition. For example, the regeneration of the catalyst composition may comprise contacting deactivated catalyst with a regeneration solution. In preferred embodiments, the regeneration solution may comprise water, more preferably deionized water. The catalyst composition may be regenerated by washing the catalyst composition with water, preferably distilled water, which is at a temperature between about 90° C. and 100° C., preferably at about 96° C., with an approximate flow of 8-10 ml/min, preferably 9 ml/min. The catalyst regeneration may be performed to remove impurities deposited and/or adsorbed on and within the OH active centers of the catalyst composition. In preferred embodiments, the regenerated catalyst composition is maintained at a constant volume throughout the aldol condensation reaction.

In some embodiments, the process for producing DAA may also comprise purifying the crude DAA recovered from the aldol condensation reaction using conventional techniques, which are known to the skilled person, to form the DAA final product. In additional or alternative embodiments, the DDA may then be dehydrated using conventional techniques, which are known to the skilled person, to yield MO.

In one embodiment, an inert or reactive gas may be supplied to the reactant stream. Examples of inert gases include, but are not limited to, nitrogen, helium, argon, and methane. Examples of reactive gases or vapors include, but are not limited to, oxygen, carbon oxides, sulfur oxides, and alkyl halides. When reactive gases such as oxygen are added to the reactor, these gases, in some embodiments, may be added in stages throughout the catalyst bed at desired levels as well as feeding with the other feed components at the beginning of the reactors.

In one embodiment, the unreacted components such as the acetone or DMK as well as the inert or reactive gases that remain are recycled to the reactor after sufficient separation from the desired product, e.g., the DDA.

The acetone or DMK conversion, in some embodiments, may vary depending upon the reaction temperature and the catalyst composition form, e.g., granular, extrudate, and amorphous forms. In one embodiment, for example, when the reaction temperature is between 1° C. and 20° C., the acetone or DMK conversion is at least 8%, e.g., between 8.0% and 15%. The selectivity to DAA is maintained at, for example, at least 86%, e.g., between 86% and 97%. Accordingly, the productivity, e.g., the space time yield, of DAA is at least 85 grams per liter catalyst per hour, e.g., at least 40 grams per liter catalyst, or at least 140 grams per liter of catalyst, when the reaction temperature is between 1° C. and 20° C. The selectivity to MO is maintained at, for example, at least 4%, e.g., between 4% and 10%. Accordingly, the productivity, e.g., the space time yield, of MO is at least 8 grams per liter catalyst per hour, e.g., at least 3 grams per liter catalyst, or at least 14 grams per liter of catalyst, when the reaction temperature is between 1° C. and 20° C.

In another embodiment where the reaction temperature is between 5° C. and 15° C., the acetone or DMK conversion is at least 8%, e.g., between 9.0% and 14.5%. The selectivity to DAA is maintained at, for example, at least 95%, e.g., between 95% and 97%. Accordingly, the productivity, e.g., the space time yield, of DAA is at least 90 grams per liter catalyst per hour, e.g., at least 55 grams per liter catalyst, or at least 135 grams per liter catalyst, when the reaction temperature is between 5° C. and 15° C. The selectivity to MO is maintained at, for example, at least 4%, e.g., between 4% and 10%. Accordingly, the productivity, e.g., the space time yield, of MO is at least 3 grams per liter catalyst per hour, e.g., at least 2 grams per liter catalyst, or at least 13 grams per liter catalyst, when the reaction temperature is between 5° C. and 15° C.

As noted above, the inventive catalyst compositions surprisingly provides for a catalyst that substantially maintains or provides for an increase in enol or enolate ion conversion in an aldol condensation reaction along with an increase in β-hydroxyaldehydes, β-hydroxyketones, and/or conjugated enone selectivity and regeneration of the inventive catalyst composition, e.g., DAA and/or MO. As a result, aldol condensation productivity is improved, as compared to conventional aldol condensation productivity with conventional catalysts, which are prepared using significant portions of sodium hydroxide, kieselghur, carbon, alumina, and/or sodium metasilicate.

EXAMPLES

The present invention may be better understood in view of the following non-limiting examples.

Process Example

Four presentations of the inventive catalyst composition in three forms (granular, extrudate, and amorphous) were prepared by mixing lime and cement in a proportion of 4:1 respectively. An industrial blender was used for mixing, and the extrudates were formed using a manual dispenser. Two granular presentations were made in the same blender, and the amorphous form was made using a mechanical press.

A first catalyst (first granular presentation) was prepared by mixing 60.0 g of portland cement with 245.5 g of lime in an industrial blender. The mixture of portland cement and lime was dosed gradually with small amounts of water to obtain a granulated material. The total of amount of water added was 104 g. The granulated material was placed in a tray to dry in an oven at a temperature of 120° C. for 18 hours to remove moisture. A remnant of 79.29 g of granulated mixture was obtained.

A second catalyst (second granular presentation) was prepared by mixing 70.76 g of portland cement with 240.26 g of lime in the industrial blender. The mixture of portland cement and lime was dosed gradually with small amounts of water to obtain a granulated material. The total of amount of water added was 116 g. The granulated material was placed in a tray to dry in an oven at a temperature of 120° C. for 18 hours to remove moisture. A remnant of 59.49 g of granulated mixture was obtained.

A third catalyst (extrudated presentation) was prepared by mixing 60.06 g of portland cement with 240.26 g of lime in the industrial blender. The mixture of portland cement and lime was dosed slowly with water to obtain a paste material. The total of amount of water added was 164 g. The paste material was placed in the manual dispenser to generate elongated cylinders of catalyst composition. The elongated cylinders were then placed on a tray to dry in an oven at a temperature of 120° C. for 18 hours to remove moisture.

A fourth catalyst (amorphous presentation) was prepared by mixing 59 g of the remnant of the second catalyst with 70.9 g of additional portland cement and 240.14 g of lime in the industrial blender. The mixture of portland cement and lime was dosed slowly with water to obtain a paste material. The total of amount of water added was 156 g. The paste material was placed on a tray to dry in an oven at a temperature of 120° C. for 18 hours to remove moisture.

Dried catalyst was selected via screening the remnants, keeping only particle sizes between 7 and 20 meshes. Four fix bed reactors connected in parallel were then loaded with the following characteristics in Table 1.

TABLE 1

| Catalyst Presentation | Weight | Volume | Bulk Density | Reactor |
| --- | --- | --- | --- | --- |
| First Catalyst (granular) | 168.24 g | 250 ml | 0.7075 | RX-1 |
| Second Catalyst (granular) | 178.52 g | 250 ml | 0.7159 | RX-2 |
| Third Catalyst (extrudate) | 136.34 g | 250 ml | 0.5598 | RX-3 |
| Fourth Catalyst (amorphous) | 172.34 g | 250 ml | 0.7172 | RX-4 |

The four presentations of the inventive catalyst composition were then activated by washing the catalyst composition with distilled water that was at a temperature of 96° C. with an approximate flow of 9 ml/min for 18 hrs. Fresh acetone with a purity of 99.1% was then fed to the reactors to maintain a space velocity of 1 hr$^{-1}$, and under the criteria of maintaining a constant 250 ml volume of catalyst within the reactors. A closed circuit system of ice water around each reactor with a constant temperature of 1° C. was used to maintain the aldol condensation reaction in isothermal conditions at approximately 1° C. As shown in FIG. 1, the system ran for 20 days with fresh acetone obtaining conversions of 14% with the granular catalyst, 13% with the amorphous catalyst, and 9% with the extrudate catalyst.

Thereafter, as also shown in FIG. 1, the reactors were fed with acetone with impurities (i.e., acetone with a purity of 97.8%) and exposed to light to induce deactivation of the catalysts, which in a time span of 8 days, lowered the catalysts conversions to 5% and 4% with the granular catalyst, 7% with the amorphous catalyst, and 2% with the extrudate catalyst. The catalysts were then regenerated, as further shown in FIG. 1, by flowing distilled water that was at a temperature of 96° C. with an approximate flow of 9 ml/min through the catalyst bed in the reactors for 18 hrs. Subsequently, the fresh acetone with a purity of 99.1% was again fed to the reactors to maintain a space velocity of 1 hr$^{-1}$, and under the criteria of maintaining a constant 250 ml volume of catalyst within the reactors. A closed circuit system of ice water around each reactor with a constant temperature of 1° C. was used to maintain the aldol condensation reaction in isothermal conditions at approximately 1° C. The system ran for an addition period of ten days. The following Table 2 shows the results of conversion and selectivities obtained with the four presentations of the inventive catalyst composition in the three stages of testing (e.g., First Stage—Addition of Fresh Acetone after Activation of the Catalysts, Second Stage—Addition of Acetone with Impurities in the Presence of Light for Deactivation, and Third Stage—Addition of Fresh Acetone After Regeneration of the Catalyst). As can be seen in Table 2, the recovery after deactivation is almost 100%.

TABLE 2

| | Conversion DMK (%) | | | Selectivity to DAA (%) | | | Selectivity to MO (%) | | |
| --- | --- | --- | --- | --- | --- | --- | --- | --- | --- |
| Catalyst | Stage 1 | Stage 2 | Stage 3 | Stage 1 | Stage 2 | Stage 3 | Stage 1 | Stage 2 | Stage 3 |
| First Catalyst (granular) | 14.407 | 4.594 | 13.714 | 88.033 | 84.552 | 87.494 | 6.983 | 3.335 | 8.868 |
| Second Catalyst (granular) | 14.154 | 5.215 | 14.352 | 88.687 | 83.782 | 87.172 | 6.524 | 3.187 | 8.798 |
| Third Catalyst (extrudate) | 9.122 | 2.077 | 10.043 | 91.869 | 50.972 | 90.808 | 3.762 | 7.683 | 4.905 |
| Fourth Catalyst (amorphous) | 13.857 | 7.048 | 13.860 | 85.761 | 87.882 | 86.834 | 8.933 | 3.247 | 9.177 |

As can be seen in Table 3, which shows the average results of conversions and selectivites of the four catalyst presentations for the first and third stages shown in Table 2, the granular and amorphous catalyst presentations had conversions equal to or better than those of conventional catalysts. The extrudate catalyst presentation was the only presentation that had lower conversions to those of conventional catalysts. However, this is attributable to the fact that the extrudate catalyst presentation had the most amount of water added in the preparation of the catalyst, which yielded a much lower overall density of the catalyst composition as compared to the other three presentations. Consequently, loading the reactors with equal volumes (i.e., 250 ml) of each catalyst left the third reactor comprising the extrudate catalyst presentation with the least mass of catalyst for the aldol condensation reaction.

TABLE 3

| Catalyst Presentation | Conversion DMK (%) | Selectivity to DAA (%) | Selectivity to MO (%) |
|---|---|---|---|
| First Catalyst (granular) | 13.8772 | 87.7635 | 7.9252 |
| Second Catalyst (granular) | 14.2529 | 87.9294 | 7.6609 |
| Third Catalyst (extrudate) | 9.5829 | 91.3385 | 4.3333 |
| Fourth Catalyst (amorphous) | 13.8568 | 86.2973 | 9.0549 |

Comparative Example

The inventive catalyst was prepared in an extruded form similarly to the processes described above with respect to the Process Example by mixing lime and cement in a proportion of 4:1 respectively. Additionally, a conventional catalyst was prepared in two extruded forms having a ⅛ inch diameter and 1/16 inch diameter by mixing sodium metasilicate, calcium hydroxide, and magnesium hydroxide. The inventive catalyst and the conventional catalysts were then exposed to deionized water for activation and acetone for aldol condensation reaction similarly to the processes described above with respect to the Process Example.

As shown in Table 4, the conversion of acetone to DAA with ⅛ and 1/16 diameter-extruded catalysts were within expected values with a slightly higher conversion for the 1/16 diameter-extruded catalyst (e.g., approximately 0.88% on average) with respect to the ⅛ diameter-extruded catalyst. For the inventive catalyst comprising cement and lime, the conversion difference was less than 1.2% on average with respect to the ⅛ diameter-extruded catalyst. This difference is due to particle size used for the inventive catalyst that established between a ¼ and ⅛ inch diameter, e.g., between −3/+7 mesh, which is a very thick material with much less contact surface than used for the conventional catalyst. Accordingly, the reduction or elimination of metasilicate in catalyst preparation and/or the replacement thereof with portland cement not only substantially maintains acetone conversion, but surprisingly and unexpectedly provides for improvements in DAA selectivity. In addition, as shown in Table 4, the improved conversions are maintained while selectivites to DAA are surprisingly and unexpectedly improved. As a result of substantially maintaining acetone conversion and the improvements in selectivity to DAA, higher productivities, e.g., space time yields, are capable in aldol condensation reactions using the inventive catalyst.

TABLE 3

| Catalyst | Conversion DMK (%) | Selectivity to DAA (%) |
|---|---|---|
| Cement and lime of present invention | 9.434 | 96.88 |
| Extruded ⅛ metasilicate and lime | 10.920 | 94.75 |
| Extruded 1/16 metasilicate and lime | 11.535 | 94.94 |

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that aspects of the invention and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

We claim:

1. A catalyst composition comprising:
    an active phase comprising lime; and
    a support comprising cement,
    wherein the lime and the cement are added to a catalyst precursor mixture that is formed into the catalyst composition in a weight ratio of at least 3.5:1 respectively.

2. The composition of claim 1, wherein the composition consists essentially of the lime, the cement, and water, and the lime comprises $Ca(OH)_2$.

3. The composition of claim 1, wherein the composition comprises particles and the particles have a particle size between about −7/+20 mesh.

4. The composition of claim 1, wherein the cement comprises $CaO$, $SiO_2$, $Al_2O_3$, and/or mixtures thereof.

5. The composition of claim 1, wherein the composition is in granular form.

6. The composition of claim 1, wherein the composition is in extrudate form.

7. The composition of claim 1, wherein the composition is in amorphous form.

8. A process for producing a catalyst composition, the process comprising the steps of:
    mixing lime and cement while providing a predetermined amount of water to form a catalyst precursor mixture; and
    drying the catalyst precursor mixture to form the catalyst composition comprising an active phase comprising the lime and a support comprising the cement,
    wherein the mixing comprises the step of adding the lime and the cement at a weight ratio of at least 3.5:1 respectively.

9. The process of claim 8, wherein the drying is performed at a temperature between about 80° C. and 160° C.

10. The process of claim 9, wherein the drying is performed at a temperature between about 110° C. and 130° C.

11. The process of claim 8, further comprising sieving the catalyst composition to obtain the catalyst composition with a particle size between about −7/+20 mesh.

12. A process for producing diacetone alcohol, the process comprising the steps of:
    reacting acetone over a catalyst composition and under conditions effective to form a crude diacetone alcohol composition, wherein the catalyst composition comprises an active phase comprising the lime and a support comprising the cement, wherein the lime and the cement are added to a catalyst precursor mixture that is formed into the catalyst composition in a weight ratio of at least 3.5:1 respectively.

13. The process of claim 12, further comprising activating the catalyst composition prior to the reacting step.

14. The process of claim 13, wherein the activating comprises the step of adding water to the catalyst composition.

15. The process of claim 14, wherein a temperature of the water is between about 90° C. and 100° C.

16. The process of claim 13, wherein the reacting comprises the step of adding the acetone to the catalyst composition to initiate an aldol condensation reaction.

17. The process of claim 16, wherein the acetone is added at a predetermined amount to maintain a space velocity of at least 1 $hr^{-1}$.

18. The process of claim 12, wherein the catalyst composition is maintained at a constant volume throughout the reacting step.

19. The process of claim 12, further comprising regenerating the catalyst composition.

20. The process of claim 19, wherein the regenerating comprises the step of contacting deactivated catalyst with a regeneration solution comprising water.

\* \* \* \* \*